(12) United States Patent
Thompson et al.

(10) Patent No.: US 12,357,584 B2
(45) Date of Patent: Jul. 15, 2025

(54) COMPOSITION AND METHOD OF CONTROLLING INFECTIOUS DISEASES WITH FUNCTIONAL FRAGRANCES

(71) Applicant: GLOBAL BIOLIFE INC., Bethesda, MD (US)

(72) Inventors: Daryl L. Thompson, Winter Haven, FL (US); Nicholas A. Van Rees, Kirkwood, MO (US); Thomas A. Meyer, St. Louis, MO (US)

(73) Assignee: GLOBAL BIOLIFE INC., Bethesda, MD (US)

( * ) Notice: Subject to any disclaimer, the term of this patent is extended or adjusted under 35 U.S.C. 154(b) by 0 days.

(21) Appl. No.: 16/212,966

(22) Filed: Dec. 7, 2018

(65) Prior Publication Data

US 2020/0179299 A1     Jun. 11, 2020

(51) Int. Cl.
| | | |
|---|---|---|
| *A61K 31/015* | (2006.01) | |
| *A61K 9/08* | (2006.01) | |
| *A61K 31/045* | (2006.01) | |
| *A61K 31/05* | (2006.01) | |
| *A61K 31/085* | (2006.01) | |
| *A61K 31/11* | (2006.01) | |
| *A61K 31/35* | (2006.01) | |
| *A61P 31/04* | (2006.01) | |
| *A61P 31/16* | (2006.01) | |

(52) U.S. Cl.
CPC ............. *A61K 31/015* (2013.01); *A61K 9/08* (2013.01); *A61K 31/045* (2013.01); *A61K 31/05* (2013.01); *A61K 31/085* (2013.01); *A61K 31/11* (2013.01); *A61K 31/35* (2013.01); *A61P 31/04* (2018.01); *A61P 31/16* (2018.01)

(58) Field of Classification Search
CPC .. A61K 31/352; A61K 31/353; A61K 31/015; A61K 31/045; A61K 31/05; A61K 31/085; A61K 31/11; A61K 31/35; A61K 9/0014; A61K 9/08; A61K 2300/00; A61P 31/04; A61P 31/16; Y02A 50/30
USPC ........................................................ 514/456
See application file for complete search history.

(56) References Cited

U.S. PATENT DOCUMENTS

| | | |
|---|---|---|
| 8,865,230 B2 | 10/2014 | Enan |
| 2006/0024393 A1 | 2/2006 | Squires |
| 2008/0145462 A1 | 6/2008 | Enan |
| 2012/0316248 A1 | 12/2012 | Enan |
| 2013/0289103 A1 | 10/2013 | Tesse |
| 2013/0324597 A1 | 12/2013 | Tesse |
| 2016/0296479 A1 | 10/2016 | Tesse |
| 2017/0000762 A1 | 1/2017 | Tesse |
| 2018/0369192 A1 | 12/2018 | Green et al. |

FOREIGN PATENT DOCUMENTS

WO    WO-2018222924    12/2018

OTHER PUBLICATIONS

Leite et al. (Brazilian, Journal of Pharmaceutical Sciences vol. 43, n. 1, Jan./Mar. 2007; Inhibitory effect of β-pinene, α-pinene and eugenol on the growth of potential infectious endocarditis causing Gram-positive bacteria ).*
Swamy et al. (Evid Based Complement Alternat Med. 2016; 2016: 3012462. Published online Dec. 20, 2016. doi: 10.1155/2016/3012462, Antimicrobial Properties of Plant Essential Oils against Human Pathogens and Their Mode of Action: An Updated Review).*
Zengin et al. (Molecules. Nov. 3, 2014;19(11):17773-98. doi: 10.3390/molecules191117773, Antibacterial and antioxidant activity of essential oil terpenes against pathogenic and spoilage-forming bacteria and cell structure-activity relationships evaluated by SEM microscopy).*
International Preliminary Report on Patentability dated Jun. 8, 2021 in International Application No. PCT/US19/64254.
Indian Office Action for IN 202117025292 dated Mar. 24, 2022.
Extended European Search Report dated Jul. 28, 2022 in European Application No. 19893270.9.
Notice of Reasons for Refusal dated Jul. 5, 2022 in Japanese Application No. 2021-532322.
Gudrun, Lang et al, "A review on recent research results (2008-2010) on essential oils as antimicrobials and antifungals. A review.", Jan. 1, 2012, pp. 13-39, vol. 27, No. 1, Flavour and Fragrance Journal, XP55044891.
Abhinav, Upadhyay, et al. "Combating Pathogenic Microorganisms Using Plant-Derived Antimicrobials: A Minireview of the Mechanistic Basis", Jan. 1, 2014, pp. 1-18, vol. 2014, BioMed Research International, XP55592227.
Barbieri, Ramona, et al, "Phytochemicals for human disease: An update on plant-derived compounds antibacterial activity", Dec. 19, 2016, pp. 44-68, vol. 196, Microbiological Research, Fischer, Jena, DE, XP029906207.
Winska, Katarxyna, et al, "Essential Oils as an Antimicrobial Agents—Myth or Real Alternative?", Sep. 5, 2016, p. 2130, vol. 24, No. 11, Molecules, XP55800965.
International Search Report dated Feb. 5, 2020 in International Application No. PCT/US19/64254.
Written Opinion dated Feb. 5, 2020 in International Application No. PCT/US19/64254.

\* cited by examiner

*Primary Examiner* — Bethany P Barham
*Assistant Examiner* — Ayaan A Alam
(74) *Attorney, Agent, or Firm* — Stephen J. Weyer, Esq.; Stites & Harbison, PLLC

(57) ABSTRACT

A composition comprises β-pinene, borneol, cinnamic aldehyde, citral, d-limonene, eucalyptol, eugenol, farnesol, linalool, thymol, and vanillin. In addition, a method for use of the composition as an antibacterial and antiviral agent is also disclosed.

16 Claims, No Drawings

COMPOSITION AND METHOD OF CONTROLLING INFECTIOUS DISEASES WITH FUNCTIONAL FRAGRANCES

FIELD OF THE INVENTION

The present invention relates to a composition and method for controlling infectious diseases, and in particular, a composition and method which includes several different functional constituents.

BACKGROUND OF THE INVENTION

Infectious diseases are a widespread and increasing problem. Bacteria, viruses, fungi, and parasites are prevalent in the environment including what one touches, what one drinks and eats, even breathes. While many are harmless or even beneficial there are some that are very harmful and cause infectious diseases, which result in sickness and death. Infectious diseases cause a third of all deaths worldwide.

Infectious diseases affect all people globally and are especially dangerous among vulnerable populations including those in the developing world, the very young, the elderly, and people undergoing treatment for other medical conditions. Infectious diseases are of particular concern in hospitals and are common in elderly care facilities leading to poor quality of life, susceptibility to other ailments, complications of existing conditions, and death.

Methicillin-resistant *S. aureus* (MRSA), antibiotic-resistant *P. aeruginosa*, and enterobacteriaceae such as *E. coli*, and *K. pneumonia* are among the most dangerous bacteria indicated as priority by the World Health Organization for development of new treatments. Antibiotics, the current standard of care for bacteria-caused infectious diseases, are becoming less effective as bacteria develop resistance to treatments through evolutionary mutations such as production of secretions that break down antibiotics and changes of structure in ways that preclude antibiotic entry or attachment.

Ways to defeat bacteria include inhibition of replication, inhibition of biofilm formation, and inhibition of quorum sensing. To inhibit the replication of bacteria an antibacterial can interfere with the process by which bacteria thrive and reproduce. To inhibit the formation of biofilm of bacteria an antibacterial can interfere with the processes by which bacteria attach to themselves or other surfaces. To inhibit quorum sensing an antibacterial can interfere with the processes by which bacteria transmit, receive, and respond to information.

Viruses such as norovirus, herpes, and the many types of influenza and rhinoviruses are persistent global health concerns, despite all current preventive measures. Influenza alone is estimated to cause between 3 and 5 million infections and between 300,000 and 650,000 deaths annually.

Ways to defeat viruses include inhibition of viral entry, inhibition of replication, and inhibition of budding and release. To inhibit viral entry an antiviral can impede the ability of a virus to infect a host cell though disruption of ICAM-1 or helicase. To reduce or prevent viral replication an antiviral can disrupt the production or use of polymerase or proteases. To prevent release of the virus progeny an antiviral can interfere with the production or use of neuraminidase.

Fungi are a responsible for multiple pathogenic infections. There are about 300 fungi that make people sick. Fungal infections can cause complications in patients receiving treatment for other diseases, can result in serious illness and can cause death.

Ways to defeat fungi or control fungus infections include inducing apoptosis and prevention or reduction of the release of harmful toxins. To induce apoptosis an antifungal can activate metacaspases, spur production of reactive oxygen species, cause disintegration of cellular ultrastructure, cause DNA fragmentation and trigger phosphatidylserine externalization. To reduce or prevent the biosynthesis of harmful toxins an antifungal can down regulate the expression of the aflR, aflT, aflD, aflM, and aflP biosynthesis toxin genes.

Parasites such as *P. falciparum* are extremely dangerous and cause Malaria, a disease that is estimated to cause over 212 million infections and over 400,000 deaths annually.

Ways to defeat parasites such as *P. falciparum* include interruption of the systems used to metabolize nutrients into energy and interference with enzymatic functions. To interrupt the metabolism an antiparasitic can inhibit the biosynthesis of isoprenoids. To interfere with enzymatic functions an antiparasitic can target key enzymes for inhibition such as the plasmepsin II enzyme.

Tuberculosis is the leading cause of deaths from a single infectious agent. *M. tuberculosis*, the bacteria that causes the disease, is spread through the air by people currently infected when they cough, sneeze, or otherwise eject infected fluids into the air. Tuberculosis caused over 1.6 million deaths and over 10 million illnesses in 2016, making it the ninth leading cause of deaths worldwide.

Ways to defeat *M. tuberculosis* include direct inhibition of the pathogen and inhibiting the biofilm and quorum sensing functions. To directly inhibit *M. tuberculosis* an antimicrobial can degrade the cellular wall of the pathogen. To inhibit the biofilm and quorum sensing functions an antimicrobial can target the genes and proteins used in these functions.

SUMMARY OF THE INVENTION

The present invention is directed to a composition and method to address the negative effects of microbial pathogens through fragrance. Contemplated is a means to combine specific substances that are known to be Generally Recognized As Safe (GRAS) for human use into fragrances for synergistic effects against microbials such as bacteria, viruses, fungi, and parasites. Using fragrant chemicals with these properties allow many commonly used products including soaps, lotions, detergents, shampoos, perfumes, body sprays, fabric softeners, and dryer sheets to be used as effective and safe antimicrobial delivery agents.

The present invention, in one form thereof, relates to a composition comprising:

0.25-7% β-pinene,
0.25-25% borneol,
5-30% cinnamic aldehyde,
0.25-25% citral,
0.25-5% d-limonene,
1-10% eucalyptol,
1-15% eugenol,
10-30% farnesol,
25-50% linalool,
0.5-7% thymol, and
2-7% vanillin.

In one specific form of the composition, the constituents are as follows:

0.25-3% β-pinene,
0.25-25% borneol, 10-25% cinnamic aldehyde,
0.25-5% citral,
0.25-5% d-limonene,
1-8% eucalyptol,
5-15% eugenol,
20-30% farnesol,
25-50% linalool,
0.5-7% thymol, and
5-20% vanillin.
In an alternative form, the composition comprises:
3-7% β-pinene,
1-5% borneol,
5-20% cinnamic aldehyde,
1-5% citral,
1-5% d-limonene,
5-10% eucalyptol,
10-15% eugenol,
10-20% farnesol,
30-50% linalool,
2-7% thymol, and
5-20% vanillin.
In still yet another form, the composition comprises:
0.5-5% β-pinene,
1-5% borneol,
10-30% cinnamic aldehyde,
1-5% citral,
1-5% d-limonene,
1-5% eucalyptol,
1-7% eugenol,
20-25% farnesol,
25-50% linalool,
0.5-2% thymol, and
2-7% vanillin.
In still yet another form, the composition comprises:
1-3% β-pinene,
1-5% borneol,
15-25% cinnamic aldehyde,
1-3% d-limonene,
5-10% eucalyptol,
5-15% eugenol,
25-50% linalool,
0.5-2% thymol, and
5-10% vanillin.

The present invention, in another form, relates to a method that treats or limits the occurrence of infectious diseases by administering a therapeutically effective amount of a composition comprising:
0.25-7% β-pinene,
0.25-25% borneol,
5-30% cinnamic aldehyde,
0.25-25% citral,
0.25-5% d-limonene,
1-10% eucalyptol,
1-15% eugenol,
10-30% farnesol,
25-50% linalool,
0.5-7% thymol, and
2-7% vanillin.

In one advantageous form, the method treats infectious diseases such as *E. coli*, MRSA, influenza and rhinovirus.

In various alternative forms, a method for treating or limiting the occurrence of limited infectious diseases comprises administering any of the aforementioned compositions.

It is envisioned that the present compositions can be used for topical application on a patient or as a surface disinfectant. Further, the compositions can be formulated to take advantage of the microbial properties of the constituent (i.e., fragrances) for administration in the olfactory and respiratory systems, for example being formulated as a liquid or mist. The presence of these antimicrobial fragrances in nasal and respiratory passages provide sufficient sites for interaction with pathogens by the antimicrobial fragrances and thereby controlling or eliminating infectious diseases.

Further, the presently disclosed compositions can be formulated as a spray, mist or otherwise release these fragrances into the air to be a layer of protection from infectious diseases caused by microbes by means of air-to-air contact with microbes yielding beneficial effects and increased safety.

Further, the presently disclosed compositions can be formulated for deployment in various applications which include use in wide open areas of airports, hospitals, triage centers, rapid response centers, and bio-defense response locations to combat the spread of severe epidemics caused by pathogens such as Ebola and Marburg through inhibition of protease, helicase, and neuraminidase.

In addition, the compositions can be used for various applications such as in travel convergence spaces such as airports, airplanes, cruise ships, ports of entry, checkpoints, and ports of exit to prevent or reduce the spread of tuberculosis.

DETAILED DESCRIPTION

The present invention is directed to unique compositions which comprise several different constituents, many of which are classified as "fragrances". In one form, the composition has the following constituents in the amounts as follows:
0.25-7% β-pinene,
0.25-25% borneol,
5-30% cinnamic aldehyde,
0.25-25% citral,
0.25-5% d-limonene,
1-10% eucalyptol,
1-15% eugenol,
10-30% farnesol,
25-50% linalool,
0.5-7% thymol, and
2-7% vanillin.
In an alternative form, the composition has the following constituents:
0.25-3% β-pinene,
0.25-25% borneol,
10-25% cinnamic aldehyde,
0.25-5% citral,
0.25-5% d-limonene,
1-8% eucalyptol,
5-15% eugenol,
20-30% farnesol
25-50% linalool,
0.5-7% thymol, and
5-20% vanillin.
In yet another form, the composition has the following constituents:
3-7% β-pinene,
1-5% borneol,
5-20% cinnamic aldehyde,
1-5% citral,
1-5% d-limonene,
5-10% eucalyptol,
10-15% eugenol,
10-20% farnesol, 30-50% linalool,
2-7% thymol, and
5-20% vanillin.

In still yet another form, the composition has the following constituents:
0.5-5% β-pinene,
1-5% borneol,
10-30% cinnamic aldehyde,
1-5% citral,
1-5% d-limonene,
1-5% eucalyptol,
1-7% eugenol,
20-25% farnesol,
25-50% linalool,
0.5-2% thymol, and
2-7% vanillin.

In yet another form, the composition has the following constituents:
1-3% β-pinene,
1-5% borneol,
15-25% cinnamic aldehyde,
1-3% d-limonene,
5-10% eucalyptol,
5-15% eugenol,
25-50% linalool,
0.5-2% thymol, and
5-10% vanillin.

These compositions have unique antimicrobial and antiviral properties. The compositions can be formulated to treat or limit the occurrence of various diseases and to kill and/or be used as a disinfectant against various microbes, pathogens, and the like. For example, the compositions can be used to kill microbes as a disinfectant and to be administered to a patient to treat a respective disease or condition. The composition has effectiveness against various pathogens including but not limited to *E. coli*, MRSA influenza, rhinovirus and *M. tuberculosis*.

The compositions can be formulated in various forms for use by a patent and can be used as a surface disinfectant. Accordingly, the compositions can be formulated as a spray or mist for surface applications. Further, the compositions can be formulated for topical use on a patient. In yet another form, the formulations can be in a liquid or mist form for olfactory or respiratory systems.

EXAMPLES

The following examples provide additional understanding of the present compositions and their uses. These examples are not to limit the scope of the disclosure in any way.

Example 1

Inhibition of bacterial quorum sensing is accomplished by terpenes such as β-pinene, citral, d-limonene and by phenols such as vanillin in ways such as inhibition of the AHL system as observed against bacteria species such as *E. coli* and *P. putida*, and by phenols such as cinnamic aldehyde and eugenol by binding to quorum sensing receptors such as RpfF, LuxS, LuxR, LasR, ExpL, and ExpR as observed against bacteria species such as *P. fluorescens, V. harveyi*, and *P. aeruginosa*.

Example 2

Inhibition of bacterial replication is accomplished by terpenes such as citral as observed against bacteria species such as *C. sakazakii*.

Example 3

Inhibition of bacterial biofilm formation is accomplished by phenols such as cinnamic aldehyde, eugenol, thymol, and vanillin and also terpenes such as citral, farnesol, and linalool as observed against bacteria species such as *C. sakazakii, S. pyogenes, S. aureus* (including methicillin-resistant strain), *A. baumannii, S. saintpaul, S. enteritidis, E. coli, V. anguillarum, Vibrio* spp., and *V. vulnificus*.

Example 4

Additionally, terpenes such as β-pinene, borneal, citral, d-limonene, farnesol, and linalool, as well as phenols such as eugenol, thymol and vanillin have efficacy against bacteria species such as *E. coli, P. aeruginosa, P. mirabilis, K. pneumoniae, A. baumannii, S. aureus, E. faecalis*, and *B. subtilis*.

Example 5

Inhibition of viral entry can be accomplished by terpenes such as eucalyptol, which inhibit the ICAM-1 molecule as observed against influenza-virus-induced pneumonia.

Example 6

Inhibition of viral replication is accomplished by terpenes such as β-pinene, borneol, citral, d-limonene and also phenols such as cinnamic aldehyde and eugenol as observed against viral pathogens such as HSV-1, influenza A/PR/8, influenza A, yellow fever, MNV-1 (human norovirus surrogate).

Example 7

Inhibition of virus progeny release is accomplished by phenols such as vanillin, which inhibit the neuraminidase enzyme.

Example 8

Induction of fungal apoptosis is accomplished by activation of metacaspases, production of reactive oxygen species, causing disintegration of cellular ultrastructure, causing DNA fragmentation and triggering externalization of phosphatidylserine by terpenes such as farnesol and linalool as observed against fungi such as *P. expansum*.

Example 9

Inhibition of biosynthesis of harmful toxins by fungi is accomplished by down regulating the expression of the aflR, aflT, aflD, aflM, and aflP biosynthesis toxin genes by phenols such as cinnamic aldehyde and eugenol and also by terpenes such as citral and farnesol against fungi such as *A. flavus*.

Example 10

Interrupting the metabolism systems of parasites by preventing or reducing the biosynthesis of isoprenoids is accomplished by terpenes such as d-limonene, farnesol, and linalool as observed against the parasite *P. falciparum*.

Example 11

Interfering with enzymatic functions of parasites by targeting enzymes such as the plamepsin II enzyme is accomplished by phenols such as thymol against the parasite *P. falciparum*.

Example 12

Directly inhibiting *M. tuberculosis* by degrading the cellular wall of *M. tuberculosis* is accomplished by terpenes such as β-pinene, d-limonene, and linalool as well as phenols such as cinnamic aldehyde, eugenol and thymol.

Example 13

Inhibition of biofilm and quorum sensing functions by targeting LuxR like genes and proteins of *M. tuberculosis* can be accomplished by terpenes such as β-pinene, d-limonene and linalool as well as by phenols such as cinnamic aldehyde, eugenol, and thymol.

PREFERRED EMBODIMENTS

The following examples of preferred embodiments are provided for additional understanding of the present compositions.

In one preferred embodiment, hereafter referenced as F1, a composition consists of not more than 5% and not less than 0.5% β-pinene, not more than 5% and not less than 1% bomeol, not more than 30% and not less than 10% cinnamic aldehyde, not more than 5% and not less than 1% citral, not more than 5% and not less than 1% d-limonene, not more than 5% and not less than 1% eucalyptol, not more than 7% and not less than 1% eugenol, not more than 25% and not less than 20% farnesol, not more than 50% and not less than 25% linalool, not more than 2% and not less than 0.5% thymol, and not more than 7% and not less than 2% vanillin.

In another composition, hereafter referenced as F2, consists of not more than 3% and not less than 0.25% β-pinene, not more than 3% and not less than 0.25% borneol, not more than 25% and not less than 10% cinnamic aldehyde, not more than 5% and not less than 0.25% citral, not more than 5% and not less than 0.25% d-limonene, not more than 8% and not less than 1% eucalyptol, not more than 15% and not less than 5% eugenol, not more than 30% and not less than 20% farnesol, not more than 50% and not less than 25% linalool, not more than 2% and not less than 0.5% thymol, and not more than 10% and not less than 5% vanillin.

In yet another composition, hereafter referenced as F3, consists of not more than 7% and not less than 3% β-pinene, not more than 5% and not less than 1% borneol, not more than 20% and not less than 5% cinnamic aldehyde, not more than 5% and not less than 1% citral, not more than 5% and not less than 1% d-limonene, not more than 10% and not less than 5% eucalyptol, not more than 15% and not less than 10% eugenol, not more than 20% and not less than 10% farnesol, not more than 50% and not less than 30% linalool, not more than 7% and not less than 2% thymol, and not more than 20% and not less than 5% vanillin.

Independent assays of the preferred embodiments F1, F2, and F3 generate the following results:

| | F1 $MIC_{99}$ | F2 $MIC_{99}$ | F3 $MIC_{99}$ |
|---|---|---|---|
| Human Rhinovirus Type 1A A/PR/8/34 | <.02% | <.02% | <.02% |
| Influenza Type A 1A2060 | <.02% | <.02% | <.02% |
| *E. coli* 25922 | 0.39% | 0.78% | 0.39% |
| *S. Aureus* (MRSA) 14154 | 0.39% | 0.39% | 0.2% |

$MIC_{99}$ is the observed minimum inhibitory concentration of the test article to eliminate 99% of the pathogen.

For the purposes of promoting an understanding of the principles of the invention, the invention has been explained in relation to various embodiments, it is to be understood that various modifications thereof will be apparent to those skilled in the art upon reading the specification. The features of the various embodiments of the articles described herein may be combined within an article. Therefore, it is to be understood that the invention described herein is intended to cover such modifications as fall within the scope of the appended claims.

What is claimed is:

1. A composition comprising:
0.25-7% β-pinene,
0.25-25% borneol,
5-30% cinnamic aldehyde,
0.25-25% citral,
0.25-5% d-limonene,
1-10% eucalyptol,
1-15% eugenol,
10-30% farnesol,
25-50% linalool,
0.5-7% thymol, and
2-7% vanillin.

2. A composition comprising:
0.25-3% β-pinene,
0.25-25% borneol,
10-25% cinnamic aldehyde,
0.25-5% citral,
0.25-5% d-limonene,
1-8% eucalyptol,
5-15% eugenol,
20-30% farnesol,
25-50% linalool,
0.5-7% thymol, and
5-20% vanillin.

3. A composition comprising:
3-7% β-pinene,
1-5% borneol,
5-20% cinnamic aldehyde,
1-5% citral,
1-5% d-limonene,
5-10% eucalyptol
10-15% eugenol,
10-20% farnesol,
30-50% linalool
2-7% thymol, and
5-20% vanillin.

4. The composition of claim 1, comprises:
0.5-5% β-pinene,
1-5% borneol,
10-30% cinnamic aldehyde,
1-5% citral,
1-5% d-limonene,
1-5% eucalyptol, 1-7% eugenol,
20-25% farnesol,
25-50% linalool,
0.5-2% thymol, and
2-7% vanillin.

5. A composition comprises:
1-3% β-pinene,
1-5% borneol,
15-25% cinnamic aldehyde,
1-3% d-limonene,
5-10% eucalyptol,
5-15% eugenol,
25-50% linalool,
0.5-2% thymol, and
5-10% vanillin.

6. A method for treating infectious diseases selected from the group consisting of *E. coli*, methicillin-resistant *Staphylococcus aureus* (MRSA), influenza, rhinovirus and *M. tuberculosis* comprising administering a therapeutically effective amount of the composition of claim 1 to a patient in need of treatment therefrom.

7. A method for treating infectious diseases selected from the group consisting of *E. coli*, methicillin-resistant *Staphylococcus aureus* (MRSA), influenza, rhinovirus and *M. tuberculosis* comprising administering a therapeutically effective amount of the composition of claim 2 to a patient in need of treatment therefrom.

8. A method for treating infectious diseases selected from the group consisting of *E. coli*, methicillin-resistant *Staphylococcus aureus* (MRSA), influenza, rhinovirus and *M. tuberculosis* comprising administering a therapeutically effective amount of the composition of claim 3 to a patient in need of treatment therefrom.

9. The method of claim 6, wherein the composition comprises:
0.5-5% β-pinene,
1-5% borneol,
10-30% cinnamic aldehyde,
1-5% citral,
1-5% d-limonene,
1-5% eucalyptol,
1-7% eugenol,
20-25% farnesol,
25-50% linalool,
0.5-2% thymol, and
2-7% vanillin.

10. A method for treating infectious diseases selected from the group consisting of *E. coli*, methicillin-resistant *Staphylococcus aureus* (MRSA), influenza, rhinovirus and *M. tuberculosis* comprising administering a therapeutically effective amount of the composition of claim 5 to a patient in need of treatment therefrom.

11. The composition of claim 1, further comprises its incorporation into a formulation selected from the group consisting of soaps, lotions, detergents, shampoos, perfumes, body sprays, fabric softeners, and dryer sheets.

12. The composition of claim 1, wherein the composition is formulated as a solution for application as a spray or mist.

13. The composition of claim 2, wherein the composition is formulated as a solution for application as a spray or mist.

14. The composition of claim 3, wherein the composition is formulated as a solution for application as a spray or mist.

15. The composition of claim 4, wherein the composition is formulated as a solution for application as a spray or mist.

16. The composition of claim 5, wherein the composition is formulated as a solution for application as a spray or mist.

* * * * *